United States Patent

Navarrini et al.

[11] Patent Number: 5,589,557
[45] Date of Patent: Dec. 31, 1996

[54] FLUORINATED POLYMERS AND COPOLYMERS CONTAINING CYCLIC STRUCTURES

[75] Inventors: Walter Navarrini; Vito Tortelli, both of Milan; Alessandro Zedda, La Spezia, all of Italy

[73] Assignee: Ausimont, S.p.A., Milan, Italy

[21] Appl. No.: 441,197

[22] Filed: May 15, 1995

[30] Foreign Application Priority Data

May 19, 1994 [IT] Italy ................. 94A001011

[51] Int. Cl.$^6$ .................................. C08F 16/24
[52] U.S. Cl. .................. 526/247; 526/249; 526/255
[58] Field of Search ............................. 526/247

[56] References Cited

U.S. PATENT DOCUMENTS

| | | | |
|---|---|---|---|
| 3,418,302 | 12/1968 | Darby | 260/87.5 |
| 4,864,006 | 9/1989 | Gianetti et al. | 526/209 |
| 4,908,461 | 3/1990 | Hung | 549/455 |
| 4,910,276 | 3/1990 | Nakamura et al. | 526/247 |
| 5,182,342 | 1/1993 | Feiring et al. | 526/206 |
| 5,225,576 | 7/1993 | Navarrini et al. | 549/449 |
| 5,235,074 | 8/1993 | Navarrini et al. | 549/449 |
| 5,245,054 | 9/1993 | Navarrini et al. | 549/455 |
| 5,247,035 | 9/1993 | Besecke et al. | 526/247 |
| 5,260,492 | 11/1993 | Feirung et al. | 568/685 |
| 5,264,508 | 11/1993 | Ishibe et al. | 526/247 |
| 5,296,617 | 3/1994 | Navarrini et al. | 549/455 |
| 5,350,821 | 9/1994 | Feiring et al. | 526/247 |
| 5,475,071 | 12/1995 | Smart et al. | 526/247 |
| 5,493,852 | 2/1995 | Ishibe et al. | 526/247 |

FOREIGN PATENT DOCUMENTS

| | | |
|---|---|---|
| 0247379 | 12/1987 | European Pat. Off. . |
| 0633257 | 1/1995 | European Pat. Off. . |
| 1106344 | 3/1968 | United Kingdom .......... 526/247 |
| 9015043 | 12/1990 | WIPO . |

OTHER PUBLICATIONS

*Inorganic Chemistry*, vol. 7, No. 3, 1968, pp. 624–626, "Some Reactions of Bis(Fluoroxy)Difluoromethane", $CF_2(OF)_2$, Hohorst et al.

Primary Examiner—Joseph L. Schofer
Assistant Examiner—N. Sarofim
Attorney, Agent, or Firm—Watson, Cole, Stevens, Davis, P.L.L.C.

[57] ABSTRACT

Polymers and copolymers of one or more fluorinated dienes of structure $CFX^1=CX^2-O-CX^3X^4-O-CX^2=CX^1F$, wherein $X^1$ and $X^2$ are F, Cl or H, and $X^3$ and $X^4$ are F or $CF_3$, wherein said dienes essentially form cyclic repetitive units, the comonomers used for preparing copolymers being ethylene unsaturated fluorinated compounds.

Processes for preparing the fluorinated dienes having said structure which comprise the reaction in solution between one halogenated olefin and one hypofluorite $CX^3X^4(OF)_2$, wherein $X^3$ and $X^4$ are F or $CF_3$, and the dehalogenation or dehydrohalogenation of the linear adduct between one hypofluorite molecule and two olefin molecules. The polymers and copolymers of the invention are particularly suitable for preparing coatings for applications at high temperatures.

9 Claims, No Drawings

FLUORINATED POLYMERS AND COPOLYMERS CONTAINING CYCLIC STRUCTURES

The present invention relates to fluorinated polymers and copolymers containing cyclic structures in the main chain. Specifically the present invention relates to fluorinated polymers and copolymers containing cyclic structures obtained by cyclopolymerization of dienes.

The polymers of the invention do not show gelling phenomena during the process for preparing them. This is important, as a matter of fact the possible formation of gels would lead to polymers having mechanical, processability and solubility characteristics unsuitable to some applications. On the other hand, the separation of gels from polymeric crude products is difficult and not always possible.

The invention relates therefore in particular to fluorinated polymers and copolymers, containing said cyclic structures, thermoprocessable and having improved thermostability combined with high solubility and absence of gels.

Said polymers and copolymers can be used in particular in preparing coatings for applications at high temperatures, where it is necessary to have high thermal stability and also high solubility to obtain solutions having high concentration of polymer.

It is known in the art that polymers containing cyclic structures in the main chain can be obtained by radical polymerization of non conjugated dienes. In particular the cyclopolymerization of fluorinated non conjugated dienes is described in U.S. Pat. Nos. 3,418,302, 4,910,276 and 5,260,492.

In U.S. Pat. No. 3,418,302 it is stressed in general that the formation of non crosslinked saturated linear polymers from compounds containing two double bonds is extremely difficult and in particular how it is possible in the case of perfluorodimethylenebisvinylether with formation of cyclic structures in the main chain only on condition that the monomer is very diluted in the polymerization step, its concentration having to be lower than 12% by weight of the total monomers and diluents. In fact if the concentration of the dienic monomer is higher, gel phenomena occur which lead to the above mentioned drawbacks.

To avoid the gel formation it was suggested in the art to resort to the use of monomers having particular molecular structures.

For instance, in U.S. Pat. No. 4,910,276 it is described the cyclopolymerization of divinylic fluorinated monomers also at high concentration of the same during polymerization, but a necessary condition for its occurrence is that the monomers have two vinylic groups with different reactivity, in practice said groups must have different structure. For the homopolymers according to this invention the thermostability data show a maximum temperature of 475° C. in relation to a weight loss of 10% because of thermal effect, while as to solubility the highest value is 7%.

Likewise U.S. Pat. No. 5,260,492 describes the cyclopolymerization of non conjugated fluorinated dienes, in particular of the ω-alkenyl-vinylethers type, but also in this case monomers having unsaturated groups with different reactivity are used.

Also polymers and copolymers obtained according to the last patents do not show in general an high thermal stability. In the case of homopolymers there is indeed a thermostability just slightly higher than that of the polymers according to U.S. Pat. No. 4,910,276: the maximum attainable temperature before loosing 10% by weight because of thermal effect is about 485° C.

Moreover, in the preparation of polymers according to said patents one has, to a different extent, the rearrangement of the vinylether group with formation of acylfluoride —COF, which, as known in the art, leads to a reduction of the thermal stability of the polymers themselves. If it is desired to reduce the content of —COF of said polymers, one could resort to a subsequent fluorination process, according to what known in the art, such resort, however, would make more complex the preparation of the polymers themselves.

It has now been surprisingly and unexpectedly found that it is possible to obtain by diene cyclopolymerization linear fluorinated polymers thermally more stable than those of the prior art, the content in fluorine being same, free from gels and endowed with high solubility, if a particular class of non conjugated fluorinated dienes is used. Such dienes, contrary to what is reported in U.S. Pat. No. 4,910,276, cyclopolymerize even though they have two vinylic groups with the same reactivity. Moreover, unexpectedly, with the monomers of the invention, rearrangement phenomena and formation of —COF groups do not occur.

According to the present invention it has surprisingly and unexpectedly found that fluorinated polymers and copolymers with cyclic structures in main chain having said characteristics, can be obtained by using, as diene, bisvinyloxymethanes having the structure $CFX^1=CX^2—O—CX^3X^4—O—CX^2=CX^1F$, wherein $X^1$ and $X^2$, equal to or different from each other, are F, Cl or H; $X^3$ and $X^4$, equal to or different from each other, are F or $CF_3$.

Object of the present invention are therefore polymers and copolymers derived from one or more of said bisvinyloxymethanes forming essentially only repetitive cyclic units having the structures a) and b):

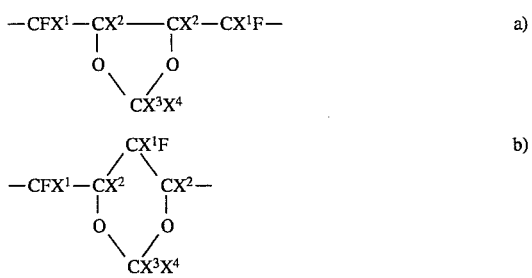

wherein $X^1$, $X^2$, $X^3$ and $X^4$ have the meaning indicated above.

In the case of copolymers, at least one of the other comonomers is a compound with an ethylene unsaturation. Utilizable comonomers of this type are olefins, optionally containing also chlorine and/or fluorine atoms, alkylvinylethers and dioxolic compounds. More precisely olefins have the structure of the type

wherein $Y^1$, $Y^2$, $Y^3$, equal to or different from each other, are F, Cl or H; Z is F, Cl, H or a perfluoroalkyl radical $R^f$ containing from one to five carbon atoms, with the proviso that the olefin contains 2 chlorine atoms at most and preferably no more than one chlorine atom; alkylvinylethers have the same structure c) wherein Z is O—$R^f$ with $R^f$ equal to a perfluoroalkylic radical having from one to five carbon atoms, with the same limitations relating to the content of chlorine atoms. The dioxolic compounds have the structure:

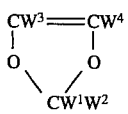

d)

wherein $W^1$ and $W^2$, equal to or different from each other, represent F or $CF_3$, $W^3$ represents F or H, and $W^4$ represents F, H, $R^f$ or $O—R^f$ with $R^f$ equal to a perfluoroalkylic radical having from 1 to 5 carbon atoms. The preparation of said dioxolic compounds is described in U.S. Pat. Nos. 4,908,461, 5,245,054, 5,296,617 when $W^4$ is different from $R^f$ and $O—R^f$. When $W^4$ is $R^f$ or $O—R^f$, for different dioxoles than the ones cited in said U.S. Pat. Nos. see the European patent application EP-A-633257.

Preferred polymers and copolymers are those derived from monomers with $X^2=X^1$, having the structure $CFX^1=CX^1—O—CX^3X^4—O—CX^1=CX^1F$, wherein $X^1$ is F, Cl or H; $X^3$ and $X^4$, equal to or different from each other, are F or $CF_3$; more preferred polymers and copolymers are those derived from monomers having the structure $CF_2=CF—O—CX^3X^4—O—CF=CF_2$, wherein $X^3$ and $X^4$, equal or different from each other, are F or $CF_3$ and even more preferred are those derived from perfluorobisvinyloxymethane $CF_2=CF—O—CF_2—O—CF=CF_2$.

As comonomers, one or more of the following compounds can be preferably used: tetrafluoroethylene, vinylidene fluoride, ethylene, chlorotrifluoroethylene, trifluoroethylene, perfluoromethylvinylether, perfluoropropylvinylether, perfluoropropene, perfluoro 2,2-dimethyl-1,3-dioxole, perfluoro 1,3-dioxole, 2,2,4-trifluoro-5-trifluoromethoxy-1,3-dioxole.

The obtained polymers show the combination of the aforesaid cyclic structures in main chain, the 5 atoms ring structures being prevalent, while both open structures containing double bonds in side chain and carbonylic groups deriving from the rearrangement of the perfluorovinylether group are substantially absent.

The polymers and copolymers according to the present invention, besides being chemically stable, have a surprising thermal stability, high transparence and in some cases, even though they have a high content in fluorine, are soluble in some common solvents, such as for instance acetone, diethyleneglycoledimethylether and N,N-dimethylformamide. The perfluorobisvinyloxymethane homopolymer and some copolymers according to this invention show on the other hand a good solubility in the fluorinated solvents, such as hydrochlorofluorocarbons, fluorohydrocarbons, perfluoroamines, perfluoroethers, similar solvents and their mixtures and high solubility in Fluorinert® FC 75 (perfluoro-2-butyl-tetrahydrofurane) and in perfluoropolyethers Fomblin® in and Galden® having, optionally, one or more H in one or in both the ending groups (e.g. $—CF_2H$).

In particular, the perfluorobisvinyloxymethane homopolymer according to this invention, has a weight loss of 10% only at a temperature of about 530° C. and it shows an high solubility in the perfluoropolyethers Fomblin® and Galden® and in Fluorinert® FC 75.

These properties make such polymers and copolymers very suitable to be used also for certain applications as protective coatings both for electric wires and particularly for metals, in applications of optical type, particularly in the manufacture of optical fibers, where the low refraction index and the high transparence of these products are used also in the area of wave lengths corresponding to the ultraviolet, and in the preparation of manufactured articles where high thermal stability is required.

The polymers and copolymers of the present invention can be prepared by radical polymerization in solution or in absence of solvent, in suspension or in mass.

General polymerization methodologies utilizable in a non aqueous medium are described for instance in U.S. Pat. Nos. 4,864,006 and 5,182,342, while methodologies utilizable in an aqueous medium are described in EP Patent 247379 and again in U.S. Pat. No. 5182342. Any substance capable of generating radicals under the chosen reaction conditions can be used as a polymerization initiator, in particular perfluoropropionylperoxide, benzoylperoxide, azobisisobutyronitrile or percarbonates can be used. It is also possible to start the polymerization using systems of redox couples, for instance those described in Prog. Polym. Sci., vol. 8, page 61, 1982.

The fluorinated derivatives of bisvinyloxymethane having the structure $CFX^1=CX^2—O—CX^3X^4—O—CX^{2'}=CX^{1'}F$, wherein $X^1$ and $X^2$, equal to or different from each other, are F, Cl or H; $X^3$ and $X^4$, equal to or different from each other, are F or $CF_3$; $X^{1'}$ and $X^{2'}$, equal to or different from each other, are $X^1$ or $X^2$, with the proviso that when $X^1$ is different from $X^2$ also $X^{1'}$ is to be different from $X^{2'}$, are new as such and are obtainable according to an innovative process. Among these compounds, those wherein $X^{1'}=X^1$ and $X^{2'}=X^2$ cyclopolymerize without giving —COF groups in the polymer; this occurs in particular in case of perfluorobisvinyloxymethane $CF_2=CF—O—CF_2—O—CF=CF_2$.

A further object of the present invention is therefore the process for preparing fluorinated derivatives of bisvinyloxymethane having the structure $CFX^1=CX^2—O—CX^3X^4—O—CX^{2'}=CX^{1'}F$, wherein $X^1$ and $X^2$ equal to or different from each other are F, Cl or H, $X^3$ and $X^4$ equal to or different from each other are F or $CF_3$, $X^{1'}$ and $X^{2'}$ equal to or different from each other are $X^1$ or $X^2$, with the proviso that when $X^1$ is different from $X^2$ also $X^{1'}$ is different from $X^{2'}$, which comprises:

i) addition of an olefin of formula $CX^1X^5=CX^2X^6$, wherein $X^1$, $X^2$, $X^5$ and $X^6$ equal to or different from each other are F, Cl, H or Br, the Br atoms being 2 at most and in such a case bound to different carbon atoms, $X^1$ and $X^5$ not being both F, $X^2$ and $X^6$ not being both F, $X^1$ and $X^2$ being F only if $X^5$ and $X^6$ are different from F and not being both H, in a reactor where an hypofluorite of general formula $CX^3X^4(OF)_2$ wherein $X^3$ and $X^4$ equal to or different from each other are F or $CF_3$, is essentially always present, dissolved in an inert solvent having a concentration comprised between 0.001M and 10M, at a temperature from −140° C. to +60° C.;

ii) separation of the reaction product between two olefin molecules and one hypofluorite molecule from the reaction mixture obtained in i) by fractional distillation.

iii) dehalogenation or dehydrohalogenation of the product obtained in ii), where the eliminated halogen atoms are Cl or Br.

The Applicant has surprisingly found experimental conditions such as to substantially and not predictably modify the reactivity of the hypofluorites having the general formula $CXY(OF)_2$ towards the olefins when one operates in solution, succeeding in obtaining with good yield linear reaction products between one molecule of hypofluorite and two molecules of olefin.

According to U.S. Pat. Nos. 5,225,576 and 5,235,074, such reactivity leads in fact essentially to the formation of a 1,3-dioxolane derivative and to the fluorination product of the olefin itself.

Linear addition products between hypofluorite and olefins in the presence of solvent are described in Inorganic Chemistry vol. 7, No. 3, 1968, page 624–6, where the hypofluorite and the olefin are first condensed in stoichiometric ratio at −184° C. and by subsequent heating they are reacted in absence of an excess of hypofluorite, conditions under which the preferred product is not the linear product but the dioxolanic compound, as described in the aforesaid patents.

The experimental conditions which surprisingly allow to obtain the linear addition product as preferred product refer to the addition methodology of the reactants used and to the polarity of the reaction medium.

It has been surprisingly found as a matter of fact that by adding the olefin to the hypofluorite dissolved in a solvent, provided that it does not react with the hypofluorite, with a concentration from 0.001M to 10M, preferably from 0.1M to 4M, at a temperature from −140° C. to +60° C. and preferably from −120° C. to 0° C., the reaction proceeds with a clear increase of the formation of the aforesaid linear reaction product. The inert solvent can be an ordinary one with low polarity, for instance dichlorodifluoromethane, trichlorofluoromethane, Fluorinert® FC 75 or a perfluoropolyether Fomblin® and Galden®, but preferably the solvent used is a polar one. The polar solvent is preferably selected from hydrogenfluorocarbons, hydrogenchlorocarbons, fluorochlorocarbons, hydrogenchlorofluorocarbons, trifluoroacetic acid, trifluoroacetic anhydride, acetic nitrile, hydrofluoric acid, sulphur dioxide, trifluoromethanesulphonic acid, $CF_2Cl$—$CFCl$—$SO_2F$, mixtures of the same and mixtures of one or more of said solvents also in small percentage with an ordinary solvent having low polarity. Among chlorinated and fluorochlorinated solvents the ones containing also hydrogen in the molecule are preferred, because of their lower impact on the decrease in the atmosphere ozone layer.

The olefin used in the process is selected depending on the desired intermediate or dienic compound. Preferred olefins are $CFCl=CFCl$, $CHCl=CHCl$, $CHCl=CCl_2$, $CCl_2=CCl_2$, $CH_2=CF_2$, $CF_2=CF_2$, $CFH=CFCl$, $CFCl=CHCl$, $CH_2=CCl_2$, $CH_2=CFCl$.

The process can be carried out both in a continuous way, introducing the olefin in a reactor where hypofluorite is always present at a concentration kept constant and in a discontinuous way by adding the olefin to an hypofluorite solution in a suitable solvent without restoring the concentration of the hypofluorite which progressively reacts.

The dehalogenation or dehydrohalogenation of the product obtained in the phase ii) of the process can be carried out according to one of the methods described in the art.

The process is preferably used for the preparation of bisvinyloxymethane derivatives having the structure $CFX^1=CX^1$—O—$CX^3X^4$—O—$CX^1=CX^1F$, wherein $X^1$ is F, Cl or H; $X^3$ and $X^4$, equal to or different from each other, are F or $CF_3$, using an olefin of formula $CX^1X^5=CX^1X^6$, where $X^1$, $X^5$ and $X^6$, equal to or different from each other, are F, Cl, Br or H, $X^1$ and $X^5$ not being both F, $X^1$ and $X^6$ not being both F, $X^1$ being Br only when $X^5$ and $X^6$ equal to each other are different from Br, $X^1$ being F only when $X^5$ and $X^6$ are different from F and not being both H.

The process is used even more preferably for the preparation of bisvinyloxymethane derivatives having the structure $CF_2=CF$—O—$CX^3X^4$—O—$CF=CF_2$, wherein $X^3$ and $X^4$, equal to or different from each other, are F or $CF_3$, using an olefin of formula $CFX^5=CFX^6$, wherein $X^5$ is Cl, Br or H, and $X^6$ is Cl or Br.

It has been found, moreover, that if the solvent used in the reaction between olefin and hypofluorite is of polar type, the addition sequence of the reactants can be inverted. A further object of the present invention is therefore a process for preparing fluorinated derivatives of bisvinyloxymethane having the structure $CFX^1=CX^2$—O—$CX^3X^4$—O—$CX^{2'}=CX^{1'}F$, wherein $X^1$ and $X^2$, equal to or different from each other, are F, Cl or H; $X^3$ and $X^4$, equal to or different from each other, are F or $CF_3$; $X^{1'}$ and $X^{2'}$, equal to or different from each other, are $X^1$ or $X^2$, with the proviso that if $X^1$ is different from $X^2$ also $X^{1'}$ is to be different from $X^{2'}$, comprising:

i) addition of hypofluorite having the general formula $CX^3X^4(OF)_2$ wherein $X^3$ and $X^4$, equal to or different from each other, are F or $CF_3$ to an olefin of formula $CX^1X^5=CX^2X^6$, wherein $X^1$, $X^2$, $X^5$ and $X^6$, equal to or different from each other, are F, Cl, H or Br; the Br atoms being 2 at most and in such a case bound to different carbon atoms; $X^1$ and $X^5$ not being both F; $X^2$ and $X^6$ not being both F; $X^1$ and $X^2$ being F only if $X^5$ and $X^6$ are different from F and not being both H; said olefin being dissolved in an inert solvent of polar type, at a temperature from −140° C. to +60° C., preferably from −120° C. to 0° C;

ii) separation of the reaction product of two olefin molecules with one hypofluorite molecule from the reaction mixture obtained in i) by fractional distillation.

iii) dehalogenation or dehydrohalogenation of the product obtained in ii), where the eliminated halogen atoms are Cl or Br.

Preferably the inert solvent of polar type is selected from hydrogenfluorocarbons, hydrogenchlorocarbons, fluorochlorocarbons, hydrogenchlorofluorocarbons, trifluoroacetic acid, trifluoroacetic anhydride, acetic nitrile, hydrofluoric acid, sulphur dioxide, trifluoromethansulphonic acid, $CF_2Cl$—$CFCl$—$SO_2F$, mixtures of the same and mixtures of one or more of said solvents also in small percentage with an ordinary low polarity solvent.

Also for this process the preferred olefins are $CFCl=CFCl$, $CHCl=CHCl$, $CHCl=CCl_2$, $CCl_2=CCl_2$, $CH_2=CF_2$, $CF_2=CF_2$, $CFH=CFCl$, $CFCl=CHCl$, $CH2=CCl_2$, $CH_2=CFCl$.

The dehalogenation or dehydrohalogenation of the product obtained in step ii) of the process can be likewise carried out according to one of the methods described in the art.

Like the previous process, also this process is preferably used for the preparation of bisvinyloxymethane derivatives having the structure $CFX^1=CX^1$—O—$CX^3X^4$—O—$CX^1=CX^1F$, wherein $X^1$ is F, Cl or H; $X^3$ and $X^4$, equal to or different from each other, are F or $CF_3$, by using an olefin of formula $CX^1X^5=CX^1X^6$ wherein $X^1$, $X^5$ and $X^6$ equal to or different from each other are F, Cl, Br or H, $X^1$ and $X^5$ not being both F, $X^1$ and $X^6$ not being both F, $X^1$ being Br only when $X^5$ and $X^6$ equal each other are different from Br, $X^1$ being F only when $X^5$ and $X^6$ are different from F and not being both H.

Likewise also this process is even more preferably used for preparing bisvinyloxymethane derivatives having the structure $CF_2=CF$—O—$CX^3X^4$—O—$CF=CF_2$, wherein $X^3$ and $X^4$, equal to or different from each other, are F or $CF_3$, using an olefin of formula $CFX^5=CFX^6$, wherein $X^5$ is Cl, Br or H, and $X^6$ is Cl or Br.

The fluorinated derivatives of bisethoxymethane obtainable after steps i) and ii) of the processes described above, possibly as a mixture of more compounds, are a further object of the present invention. These products, besides being used as intermediates for the synthesis of monomers, are also used as fluorinated solvents with low impact on the atmospheric ozone layer. The products without chlorine are preferred for this use.

The following examples are to be considered for illustrative purposes, but not limitative of the scope of the present invention.

EXAMPLES 1–16

Bisethoxymethane derivatives from olefin and hypofluorite: addition of the hypofluorite to the olefin in solvents having different polarity.

EXAMPLE 1

80 g (600 moles) of 1,2-dichloro-1,2-difluoroethylene and a solvent mixture formed by 32 g of $SO_2$ and 17 g of $CH_2Cl_2$ are introduced into a 125 ml multi-neck glass cylindrical reactor, equipped with mechanical stirrer, thermocouple, suction inlet for the reacting gaseous mixture and inert gas head outlet.

The so loaded reactor is brought to the temperature of −80° C. using a cryostat, and then a mixture of $CF_2(OF)_2$ (1,5 Nl/h), $CO_2$ (2,2 Nl/h) and helium (6 Nl/h) are continuously added under mechanical stirring for 3.5 hours with an overall supply of hypofluorite equal to 234 moles.

The reaction is practically instantaneous. When the addition of the mixture containing hypofluorite is over, the products are separated from the reaction crude product by fractional distillation with a plate column at atmospheric pressure. The fractions having boiling point in the range comprised between −1° and +1° with respect to the temperatures indicated hereinafter, are collected:

a) at +4° C. 19.3 g (112 moles) of $CF_2Cl$—$CF_2Cl$ b) at +22° C. 17.4 g (131 moles) of unreacted $CFCl$=$CFCl$ c) at 47°/49° C. mixture formed by 24.4 g (113 moles) of 4.5-dichloro-2,2,4,5-tetrafluoro-1,3-dioxolane and 4 g (22 moles) of $CClF_2$—$CCl_2F$ d) at +76° C. 8.6 g (40 moles) $CF_2Cl$—$CFCl$—$OC(O)F$ e) at +70.5° C./54 mm Hg 20.4 g (52 mmoles of $CF_2Cl$—$CFCl$—$OCF_2$—$CFCl$—$CF_2Cl$.

The linear addition product yield, defined as ratio between the obtained moles of $CF_2Cl$—$CFCl$—$OCF_2$—$CFClCF_2Cl$ and the used moles of $CF_2(OF)_2$, is 22%. The product has been characterized by $F^{19}$-NMR spectroscopy (in p.p.m. related to $CFCl_3$=: 2F type O—$CF_2$—O at −50.5/−52.0; 4F type Cl—$CF_2$—C at −70.3/−72.3; 2F type C—CFCl—O at −77.5), and electronic impact mass spectroscopy, where the main peaks and the relative intensities are: 151 (100%), 101 (23%), 85 (15%), 66 (12%), 47 (12%), 28 (33.5%).

EXAMPLE 2–11

In these examples some solvents and co-solvents are tested at different temperatures under experimental conditions comparable with the ones of example 1. The data relating to the yield in linear addition product formed by two molecules of olefin and one molecule of hypofluorite and under the experimental conditions adopted are reported in Table 1.

EXAMPLE 12

In this example the use of a different olefin, the trans-1,2-dichloroethylene, is tested.

174 g (1,79 moles) of trans-1,2-dichloroethylene and a solvent mixture formed by 118 g of $SO_2$ and 247 g of $CFCl_3$ are introduced into a 500 ml multi-neck glass cylindrical reactor, equipped with mechanical stirrer, thermocouple, suction inlet for the reacting gaseous mixture and inert gas head outlet.

The so loaded reactor is brought to the temperature of −76° C. using a cryostat, and then a mixture of $CF_2(OF)_2$ (2 Nl/h), $CO_2$ (1.0 Nl/h) and helium (6 Nl/h) are continuously added under mechanical stirring for 8.5 hours with an overall supply of hypofluorite equal to 760 moles. When the addition of hypofluorite is over, the sulphur dioxide and part of $CFCl_3$ are separated from the reaction crude product by distillation. Then the reaction products are separated by fractional distillation with a plate column at reduced pressure. The fractions having boiling point in the range between −1° and +1° with respect to the temperature indicated hereinafter, are collected:

a) at +20° C./70 mm Hg mixture of 50 g of CFClH—CFClH and 25 g of unreacted trans-1,2-dichloroethylene;

b) at +29° C./58 mm Hg 46 g of 4.5-dichloro-2,2-difluoro-1,3-dioxolane;

c) at +12° C./24 mm Hg 20 g of CFClH—CClH—OC(O)F d) at +64° C./3 mm Hg 71 g of CFClH—CHCl—$OCF_2$O—CHCl—CFClH.

The linear addition product yield, defined as ratio between the obtained moles of CFClH—CHCl—$OCF_2$O—CHCl—CFClH and the used moles of $CF_2(OF)_2$, is 30%. The product has been characterized by $F^{19}$-NMR spectroscopy (in p.p.m. related to $CFCl_3$=O: 2F type O—$CF_2$—O at −58.0/−61.5; 2F type CHFCl—CHCl— at −141/−146), $H^1$-NMR spectroscopy (in p.p.m related to TMS =0: complex multiplier at +5.6/6.9) and mass spectroscopy (main peaks: 209, 211, 213 for $C_4H_3OCl$; 179, 181, 183 for $C_3H_2OF_3Cl_2$; 131, 133, 135 for $C_2H_2OFCl$; 15, 117, 119 for $CH_2FCl_2$).

EXAMPLE 13 and 14

In these examples the use of trans-1,2-dichloroethylene is tested, with the same procedure of example 12, under different conditions reported in Table 1 along with the linear addition product yield.

EXAMPLE 15

79 g (0.6 moles) of trichloroethylene and a solvent mixture formed by 39 g of $SO_2$ and 83 g of $CFCl_3$ are introduced into a 500 ml multi-neck glass cylindrical reactor, equipped with mechanical stirrer, thermocouple, suction inlet for the reacting gaseous mixture and inert gas head outlet.

The so loaded reactor is brought to the temperature of −74° C. using a cryostat, and then a mixture of $CF_2(OF)_2$ (1 Nl/h), $CO_2$ (0.5 Nl/h) and helium (3 Nl/h) are continuously added under mechanical stirring for 6 hours.

When the addition of hypofluorite is over, solvents and most volatile reaction products $CHFCl$—$CFCl_2$ and 4,4,5-trichloro-2,2,4-trifluoro-1,3-dioxolane are stripped off the crude reaction mixture.

33 g of isomeric, essentially pure bisethereal addition products, having molecular weight 382.8, are left in the kier. The bisethereal products can be separated by gaschromatography. The characterization is reported in example 18.

The linear addition product yield, defined as ratio between the moles of obtained bisethereal products and the used moles of $CF_2(OF)_2$, is 32%.

EXAMPLE 16

100 g (0.6 moles) of tetrachloroethylene and a solvent mixture formed by 39 g of $SO_2$ and 124 g of $CFCl_3$ are introduced into a 500 ml multi-neck glass cylindrical reactor, equipped with mechanical stirrer, thermocouple, suction inlet for the reacting gaseous mixture and inert gas head outlet.

The so loaded reactor is brought to the temperature of $-54°$ C. using a cryostat, and then a mixture of $CF_2(OF)_2$ (1 Nl/h), $CO_2$ (0.5 Nl/h) and helium (3 Nl/h) are continuously added under mechanical stirring for 6 hours.

When the addition of hypofluorite is over, solvents and most volatile reaction products $CFCl_2$—$CFCl_2$ and 4,4,5,5-tetrachloro-2,2-difluoro-1,3-dioxolane are stripped off the crude reaction mixture.

32 g of the essentially pure bisethereal addition product $CFCl_2$—$CCl_2$—$OCF_2O$—$CCl_2$—$CFCl_2$ are left in the kier.

The linear addition product yield, defined as ratio between the moles of obtained bisethereal product and the used moles of $CF_2(OF)_2$, is 26%.

The product $CFCl_2$—$CCl_2$—$OCF_2O$—$CCl_2$—$CFCl_2$ is characterized by $F^{19}$-NMR spectroscopy, where it shows in p.p.m., related to $CFCl_3$=0, 2F type $OCF_2O$ at $-50.7$ and 2F type $CFCl_2$ at $-67.5$.

The mass spectroscopy analysis shows the following main peaks and relative intensities: 185 (100%), 148 (15%), 101 (12%).

TABLE 1

Formation of linear addition product between hypofluorite and olefin: addition of hypofluorite to the olefin(*)

| Ex. | Solvent (g) | | Cosolvent (g) | | Temperature (°C.) | Linear addition product yield (% by moles) |
|---|---|---|---|---|---|---|
| 1 | $SO_2$ | 32 | $CH_2Cl_2$ | 17 | $-80$ | 22.0 |
| 2 | $CH_2Cl_2$ | 8 | | | $-90$ | 10.5 |
| 3 | $SO_2$ | 32 | | | $-80$ | 18.6 |
| 4 | $SO_2$ | 19.2 | | | $-80$ | 17.5 |
| 5 | $SO_2$ | 19.2 | | | $-90$ | 8.5 |
| 6 | $SO_2$ | 19.2 | | | $-60$ | 17.0 |
| 7 | $SO_2$ | 64 | $CH_2Cl_2$ | 34 | $-80$ | 18.3 |
| 8 | $CF_2Cl$—$CFCl$—$SO_2F$ | 127 | | | $-80$ | 18.5 |
| 9 | HF | 8 | | | $-80$ | 12.4 |
| 10 | $(CF_3C(O))_2O$ | 8 | | | $-70$ | 12.0 |
| 11 | $CF_3SO_3H$ | 8 | | | $-55$ | 11.0 |
| 12 | $SO_2$ | 118 | $CFCl_3$ | 247 | $-76$ | 30.0 |
| 13 | $SO_2$ | 118 | $CH_2Cl_2$ | 153 | $-70$ | 43.0 |
| 14 | — | | $CHCl_2$—$CF_3$ | 250 | $-70$ | 36.0 |
| 15 | $SO_2$ | 39 | $CFCl_3$ | 83 | $-74$ | 32.0 |
| 16 | $SO_2$ | 39 | $CFCl_3$ | 124 | $-54$ | 26.0 |

(*)The hypofluorite is $CF_2(OF)_2$; the olefin is 1,2-dichloro-difluoroethylene in the examples from 1 to 11, trans 1,2-dichloroethylene in the examples from 12 to 14, trichloroethylene in example 15 and tetrachloroethylene in example 16.

EXAMPLE 17–22

Bisethoxymethane derivatives from olefin and hypofluorite: addition of olefin to hypofluorite.

EXAMPLE 17

2 ml of $CFCl_3$ are loaded in a 10 ml two necks glass flask equipped with magnetic stirrer and internal thermocouple.

The reactor is brought to $-196°$ C. and evacuated. Subsequently by vacuum line transfer 1 m mole of $CF_2(OF)_2$ is condensed therein at $-196°$ C. The so loaded reactor is brought to $-100°$ C. and the solution of $CF_2(OF)_2$ in $CFCl_3$ is homogenized under magnetic stirring. 3 mmoles of $CFCl$=$CFCl$ are slowly added by condensation to the so obtained 0,5 molar solution of $CF_2(OF)_2$ in $CFCl_3$ and maintained at $-100°$ C. so that the reaction heat immediately developed is effectively vented by the cooling system.

The weight percentages of the reaction products, determined by gaschromatography and by NMR, are: $CF_2Cl$—$CF_2Cl$ 40.3%; 4,5-dichloro-2,2,4,5-tetrafluoro-1,3-dioxolane 50,7%; $CF_2Cl$—$CFCl$—$OCF_2O$—$CFCl$—$CF_2Cl$ 9%. The linear addition product, defined as for example 1, is 9%.

EXAMPLE 18 and 19

Under experimental conditions comparable with those of example 17, some solvents and $CF_2(OF)_2$ concentrations are tested at different temperatures. The data relating to the linear adduct yield and to the adopted experimental conditions are reported in Table 2.

EXAMPLE 20

20 ml of $CHCl_2$—$CF_3$ (d=1.5 g/l) are loaded into a 125 ml multi-neck glass cylindrical reactor, equipped with mechanical stirrer, thermocouple, suction inlet for the reacting gaseous mixture, inlet on the reactor top for the liquid reacting olefin, inert gas head outlet. The so loaded reactor is brought to $-97°$ C. by means of a cryostat, and then a gaseous mixture of $CF_2(OF)_2$ (0.50 Nl/h), $CO_2$ (0.25 Nl/h) and He (1.5 Nl/h) is continuously introduced under mechanical stirring until a 1.5M concentration of $CF_2(OF)_2$ in solution is achieved.

At this point $CHCl$=$CCl_2$ in admixture with hypofluorite is continuously added so as to keep constant the concentration of the latter in the solution during the addition. After 4 h and 30', the addition of the gaseous mixture containing $CF_2(OF)_2$ is interrupted and the addition of $CHCl$=$CCl_2$ is continued up to the complete conversion of $CF_2(OF)_2$ dissolved in the solution.

At the end of the reaction, the reaction crude product is stripped from the solvent and from the most volatile reaction by-products: $CHFCl$—$CFCl_2$ and 4,4,5-trichloro-2,2,4-trifluoro-1,3-dioxolane. 34.5 g of a mixture of bisethereal addition products formed by:

A) 71.5% Of $CCl_2F$—$CHCl$—$OCF_2O$—$CHCl$—$CCl_2F$

B) 27.7% Of $CCl_2F$—$CHCl$—$OCF_2O$—$CCl_2$—$CHClF$

C) 0.8% of $CHClF$—$CCl_2$—$OCF_2O$—$CCl_2$—$CHClF$ are obtained as residue.

The products are separated by preparative gaschromatography. The linear addition product yield, defined as ratio between the sum of the moles of products A, B and C and the moles of $CF_2(OF)_2$ converted, is 69%.

The products are characterized by $F^{19}$-NMR spectroscopy where they show, in p.p.m., related to $CFCl_3$=0:

product A: 2F type $CFCl_2$ at $-66.5$; 2F type $OCF_2O$ at $-59.3/-61.5$;

product B: 1F type $CFCl_2$ at $-66.2$; 1F type CFHCl at $-138.3$; 2F type $OCF_2O$ at $-55.0/-56.3$;

product C: 2F type CFHCl at $-138.4$; 2F type $OCF_2O$ at $-50.6$.

The mass spectroscopy analysis shows the following main peaks and relative intensities: 151 (100%), 131 (23.5%), 114 (33%), 101 (20%), 79 (14%).

EXAMPLE 21

54 ml of $CH_2F$—$CF_3$ (d=1.2 g/l) are loaded into a 125 ml multi-neck glass cylindrical reactor, equipped with mechanical stirrer, thermocouple, suction inlet for the reacting gaseous mixture $CF_2(OF)_2/CO_2$/diluent gas, suction inlet for the reacting olefin, inert gas head outlet. The so loaded reactor is brought to −90° C. by means of a cryostat, and then a gaseous mixture of $CF_2(OF)_2$ (1.0 Nl/h), $CO_2$ (0.5 Nl/h) and He (4 Nl/h) is continuously introduced under mechanical stirring until a 0.2M concentration of $CF_2(OF)_2$ in solution is achieved.

At this point CClF=CHF (2.0 Nl/h) is continuously added so as to keep constant the concentration of the hypofluorite in the solution during the addition. After 1h and 40', the addition of the gaseous mixture containing $CF_2(OF)_2$ is interrupted and the addition of CClF=CHF is continued up to the complete conversion of $CF_2(OF)_2$ dissolved in the solution.

At the end of the reaction, the reaction crude product is stripped from the solvent and from the most volatile reaction by-products: $CHF_2$—$CF_2Cl$ and 4-chloro-2,2,4,5-tetrafluoro-1,3-dioxolane. 16.5 g of a mixture of bisethereal addition products formed by:

A) 74% Of $CClF_2$—CHF—$OCF_2O$—CHF—$CClF_2$

B) 23% Of $CClF_2$—CHF—$OCF_2O$—CClF—$CHF_2$

C) 3% of $CHF_2$—CClF—$OCF_2$ O—CClF—$CHF_2$ are obtained as residue.

The products are separated by preparative gaschromatography. The linear addition product yield, defined as ratio between the sum of the moles of products A, B and C and the moles of $CF_2(OF)_2$ converted, is 61%. The products are characterized by $F^{19}$-NMR spectroscopy and $H^1$-NMR spectroscopy.

By $F^{19}$-NMR spectroscopy the products show, in p.p.m., related to $CFCl_3$=O:

product A: 4F type $CF_2Cl$ at −71.5; 2F type CHF at −140.3; 2F type $OCF_2O$ at −58.5/−60.0;

product B: 2F type $CF_2Cl$ at −71.5; 1F type CHF at −140.3; 1F type CFCl at −81.2; 2F type $CHF_2$ at −131/−134; 2F type $OCF_2O$ at −54.0/−56.6;

product C: 2F type CFCl at −81.2; 4F type $CHF_2$ at −131/−134; 2F type $OCF_2$ O at −54.0/56.6.

By $H^1$-NMR spectroscopy the products show, in p.p.m., related to TMS=0:

product A: 2H type CHF at 5.8–6.0 product B: 1H type CHF at 5.8–6.0; 1H type $CF_2H$ at 5.7–5.9–6.1 product C: 2H type $CF_2H$ at 5.7–5.9–6.1

The electronic impact mass spectroscopy analysis shows the following main peaks and relative intensities: 185 (7%), 183 (20%), 119 (38%), 117 (100%), 67 (15%).

EXAMPLE 22

160 ml of $CH_2F$—$CF_3$ (d=1.2 g/l) are loaded into a 250 ml multi-neck glass cylindrical reactor, equipped with mechanical stirrer, thermocouple, suction inlet for the reacting gaseous mixture $CF_2(OF)_2/CO_2$/diluent gas, suction inlet for the reacting olefin, inert gas head outlet. The so loaded reactor is brought to −95° C. by means of a cryostat, and then a gaseous mixture of $CF_2(OF)_2$ (1.0 Nl/h), $CO_2$ (0.5 Nl/h) and He (4 Nl/h) is continuously introduced under mechanical stirring until a 0.05M concentration of $CF_2(OF)_2$ in solution is achieved.

At this point vinylidene fluoride $CH_2$=$CF_2$ (2.0 Nl/h) is continuously added so as to keep constant the concentration of the hypofluorite in the solution during the addition. After 2h and 40', the addition of the gaseous mixture containing $CF_2$ $(OF)_2$ is interrupted and the addition of $CH_2$=$CF_2$ is continued up to the complete conversion of $CF_2(OF)_2$ dissolved in the solution.

At the end of the reaction, 21 g of $CF_3CH_2OCF_2OCH_2CF_3$ (b.p. +51° C./200 mm Hg) are isolated by fractional distillation.

The linear addition product yield, defined as the ratio between the moles of $CF_3CH_2OCF_2OCH_2CF_3$ and the moles of $CF_2(OF)_2$ converted, is 67%. The product has $T_g$=−127.9° C. The product is further characterized by $F^{19}$-NMR spectroscopy and mass spectroscopy.

By $F^{19}$-NMR spectroscopy the product shows 2F type $OCF_2O$ at −64.0 p.p.m. and 6F type $CF_3$—$CH_2$ at −73.9 p.p.m., related to $CFCl_3$=O.

The electronic impact mass spectroscopy analysis shows the following main peaks and relative intensities: 179 (33.1%), 163 (28.2%), 149 (100%), 113 (17.7%), 83 (83.1%).

The linear adduct yield and the experimental conditions adopted in examples 17–22 are summarized in Table 2.

TABLE 2

Formation of linear addition product between hypofluorite and olefin: addition of olefin to hypofluorite(*)

| Ex. | Solvent (g) | $CF_2(OF)_2$ (moles/l) | Temperature (°C.) | Linear addition product yield (% by moles) |
|---|---|---|---|---|
| 17 | $CFCl_3$ | 0.5 | −100 | 9 |
| 18 | $CF_3$—$CFH_2$ | 2 | −95 | 19.2 |
| 19 | CFCl—CFCl—SOF | 2 | −90 | 26.1 |
| 20 | $CHCl_2$—$CF_3$ | 1.5 | −97 | 69 |
| 21 | $CH_2F$—$CF_3$ | 0.2 | −90 | 61 |
| 22 | $CH_2F$—$CF_3$ | 0.05 | −95 | 67 |

(*)The hypofluorite is $CF_2(OF)_2$; the olefin is 1,2-dichloro-difluoroethylene in the examples from 17 to 19, trichloroethylene in example 20, 1-chloro-1,2 difluoroethylene in example 21 and vinylidene fluoride in example 22.

EXAMPLE 23

Preparation of perfluorobisvinyloxymethane (dehalogenation process).

500 ml of dimethylformamide, 90 g of Zn in powder previously activated by washing with 3N HCl and 100 mg of $I_2$ are loaded into a 1 l three-neck flask, equipped with mechanical stirrer, thermometer, dripping funnel, distillation column with water cooler and collecting trap kept at −78° C. and connected to the vacuum of a mechanical pump. The internal temperature is brought to 80° C., the vacuum is adjusted at 160 mm Hg and 88.4 g (229 moles) of $CF_2Cl$—CFCl—$OCF_2O$—CFCl—$CF_2Cl$ are added in drops.

Once the addition is over, the reaction mixture is kept under the conditions indicated above for 30 minutes, and then the vacuum is gradually increased up to 0.5mm Hg. After about 20 minutes the collecting flask is disconnected; it contains 51.3 g of a mixture consisting for 89% by weight of perfluorobisvinyloxymethane $CF_2$=CF—O—$CF_2O$—CF=$CF_2$ (45.6 g equal to 187 moles) and for 11% by weight of the compound of hemidehalogenation $CF_2$=CF—O—$CF_2$—O—CFCl—$CF_2Cl$ (5.6 g equal to 18 moles). After purification by distillation at atmospheric pressure with a plate column, 42 g (172 moles) of perfluorobisvinyloxymethane having boiling point at atmospheric pressure of 50° C. are isolated. The yield is 75%.

The product was characterized by $F^{19}$-NMR spectroscopy (in p.p.m., related to $CFCl_3$=O: 2F type $CF_2$=C— at −114.0/−121.1; 1F type C=CF—O at −136.1; 2F type O—CF$_2$—O at −60.4); IR spectrum (absorption bands at 1840, 1338, 1298, 1248, 1192 cm$^{-1}$) and mass spectrum (electronic impact): 163 (M$^+$—C$_2$F$_3$); 147 (M$^+$—C$_2$F$_3$O); 135 (C$_2$F$_5$O); 119 (C$_2$F$_5$).

EXAMPLE 24

Preparation of bis-(2-fluorovinyloxy)-methane CFH=CH—OCF$_2$O—CH=CHF (dehalogenation process).

50 ml of dimethylformamide, 21 g of Zn in powder previously activated by washing with 3N HCl and 10 mg of I$_2$ are loaded into a 150 ml three necks flask, equipped with mechanical stirrer, thermometer, dripping funnel, distillation column with water cooler and collecting trap kept at −78° C. and connected to the vacuum of a mechanical pump. The internal temperature is brought to 120° C., the vacuum is adjusted at 350mm Hg and 17.7 g (56.4 moles) of CFHCl—CHCl—OCF$_2$O—CHCl—CFHCl are added in drops.

Once the addition is over, the reaction mixture is kept under the conditions indicated above for 15 hours, and then the vacuum is gradually increased up to 200mm Hg, after about 15 minutes the collecting flask containing 18.3 g of a mixture consisting of CFH=CH—OCF$_2$O—CH=CHF and dimethylformamide is disconnected.

After purification of the mixture by washing twice with water and by distillation at reduced pressure with plates column, 4.6 g (26.7 moles) of 98% pure CFH=CH—OCF$_2$O—CH=CHF having boiling point of 42.0° C. at 200 mm Hg are isolated. The yield is 47%.

The product was characterized by F$^{19}$-NMR spectroscopy where it shows in p.p.m., related to CFCl$_3$=O: 2F type O—CF$_2$—O at −62.9; −63.3; −63.7; 1F type trans F—CH=CH—O at −153.5; 1F type cis F—CH=CH—O at −168.5; mass spectrum with electronic impact, wherein the main peaks and the relative intensities are: 45 (73%), 78(17%), 111 (100%), 172 (1%); and IR spectrum wherein the following main peaks are observed: 3110, 1719, 1693, 1374, 1301, 1202, 1106 and 1028 cm$^{-1}$.

EXAMPLE 25

Preparation of perfluorobisvinyloxymethane (dehydrohalogenation process)

3 g of bisethereal addition products mixture prepared in example 21 and 100 mg of tetrabutylammonium chloride, as phase transfer catalyst, are loaded into a 100 ml three necks flask, equipped with mechanical stirrer, thermometer, dripping funnel, distillation column with water cooler and collecting trap kept at −78° C. and connected to the vacuum of a mechanical pump. The internal temperature is brought to 60° C., the vacuum is adjusted at 200 mm Hg and 3 ml of a 40% KOH water solution are added in drops.

Once the addition is over, the reaction mixture is kept under the conditions indicated above for 30', and then the vacuum is gradually increased up to 100mm Hg. After about 30' the collecting flask is disconnected; it contains 2 g of a mixture essentially consisting of perfluorobisvinyloxymethane, unreacted or only partially reacted starting product and water traces. From the crude reaction mixture, after dehydration with solid KOH, 1.3 g of perfluorobisvinyloxymethane and 0.5 g of not dehydrohalogenated products are isolated by distillation. The yield of the perfluorobisvinyloxymethane is 66%.

The product was characterized by F$^{19}$-NMR spectroscopy, IR spectroscopy and mass spectroscopy as in example 23.

EXAMPLE 26

Polymerization of perfluorobisvinyloxymethane without use of solvent.

The polymerization initiator consisting of 32 microliters of 6.5% by weight perfluoropropionylperoxide in CCl$_2$F—CF$_2$Cl and 6.4 moles of perfluorobisvinyloxymethane are loaded into a 31.2 ml glass reactor for polymerization, equipped with magnetic stirring and opening for the loading and unloading of the reactants.

The so loaded reactor is cooled to −196° C., evacuated, brought to room temperature and cooled again twice; at the end of this operations sequence the reactor is kept at 30° C. for 1 hour under magnetic stirring. The reaction crude product so obtained looks like a viscous, transparent, colourless and homogeneous solution.

After distillation of the unreacted monomer and stripping under vacuum at the temperature of 120° C. for 3 hours, 340 mg of polymer are isolated.

The infrared analysis of the obtained polymer shows the absence of absorptions in the area of the carbonyl and in the area of the fluorinated double bond.

The F$^{19}$-NMR analysis is in accordance with the presence of the cyclic structures reported above, structure a) being 89% and structure b) being 11%. Neither unreacted vinyls nor acylfluorides appear.

The intrinsic viscosity of the polymer measured in Fluorinert® FC 75 is 66 ml/g. A Differential Scanning Calorimetry (DSC) test carried out on the polymers does not show any melting point, therefore the polymer is amorphous. The polymer T$_g$ determined by DSC is 77.8° C. The thermogravimetric analysis (TGA) shows a weight loss of 2% at 488° C. and of 10% at 530° C.

EXAMPLE 27

Polymerization of perfluorobisvinyloxymethane in solution.

The polymerization initiator consisting of 50 microliters of 6.5% by weight perfluoropropionylperoxide in CCl$_2$F—CF$_2$Cl, 16.6 moles of CCl$_2$F—CF$_2$Cl and 6.4 moles of perfluorobisvinyloxymethane are loaded into a 52.3 ml glass reactor for polymerization, equipped with magnetic stirring and opening for the loading and unloading of the reactants.

The so loaded reactor is cooled to −196° C., evacuated, brought to room temperature and cooled again twice; at the end of this operations sequence the reactor is kept at 30° C. for 2 hours under magnetic stirring. The reaction crude product so obtained looks like a viscous, transparent, colourless and homogeneous solution.

After distillation of the unreacted monomer and stripping under vacuum at the temperature of 120° C. for 3 hours, 450 mg of polymer are isolated.

The infrared analysis of the obtained polymer shows the absence of absorptions in the area of the carbonyl and of the fluorinated double bond.

The F$^{19}$-NMR analysis is in accordance with the presence of the cyclic structures reported above, structure a) being 89% and structure b) being 11%. Neither unreacted vinyls nor acylfluorides appear.

The intrinsic viscosity of the polymer measured in Fluorinert® FC 75 is 56 ml/g. The solubility of this homopolymeric sample in Fluorinert® FC 75 and in perfluoropolyethers Fomblin® and Galden® is higher than 20% by weight at room temperature. The 20% by weight solutions in these solvents are very viscous, but transparent and visually homogeneous; solutions even with concentration higher than 20% by weight are extremely viscous, but substantially homogeneous. The $T_g$ of the polymer determined by DSC and the TGA are substantially the same as the $T_g$ and the TGA of the polymer obtained in example 23.

EXAMPLE 28

Copolymer of perfluorobisvinyloxymethane with vinylidene fluoride.

3 ml of $CCl_2F$—$CF_2Cl$, the polymerization initiator consisting of 32 microliters of 6.5% by weight perfluoropropionylperoxide dissolved in $CCl_2F$—$CF_2Cl$, 2.20 moles of perfluorobisvinyloxymethane and 7.8 moles of vinylidene fluoride are loaded into a 52 ml glass reactor for polymerization, equipped with magnetic stirring and opening for the loading and unloading of the reactants.

The so loaded reactor is cooled to $-196°$ C., evacuated, brought to room temperature and cooled again twice; at the end of this operation sequence the reactor is kept at 30° C. for 16 hours under magnetic stirring. The reactor is brought to the temperature of the liquid nitrogen and connected to a vacuum system kept at the pressure of $10^{-3}$ mbar, it is then let to reach room temperature fractionating the vapours by traps cooled at $-80°$ C., $-120°$ C., and $-196°$ C.

The trap at $-80°$ C. contains only the $CFCl_2$—$CF_2Cl$ used as solvent. The trap at $-120°$ C. contains 6.90 moles of $CFCl_2$—$CF_2Cl$ and 0.26 moles of unreacted perfluorobisvinyloxymethane. The trap at $-196°$ C. contains 4.5 moles of unreacted vinylidene fluoride.

After distillation of the solvent and of the unreacted monomers and stripping of the polymer under vacuum at the temperature of 120° C. for 3 hours, 670 mg of polymer are isolated.

The weight balance determined by gaschromatography analysis of the content of the traps containing the unreacted monomers allows to calculate the amount of perfluorobisvinyloxymethane in the polymer, which results to be 37% by moles. The polymer results soluble in N,N-dimethylformamide.

The F19-NMR analysis is in accordance with the presence of the cyclic structures reported above, structure a) being 91.4% and structure b) being 8.6% Neither unreacted vinyls nor acylfluorides appear.

The polymer $T_g$ determined by DSC is 17.2° C. The DSC graph does not show any melting endotherm, therefore the polymer is amorphous. The TGA shows a weight loss of 2% at 412° C. and of 10% at 450° C.

EXAMPLE 29

Copolymer of tetrafluoroethylene with perfluorobisvinyloxymethane.

8 ml of $CCl_2F$—$CF_2Cl$, the polymerization initiator consisting of 1.5 ml of 0.35% by weight perfluoropropionylperoxide in $CCl_2F$—$CF_2Cl$, 0.33 moles of perfluorobisvinyloxymethane and 10 moles of tetrafluoroethylene are loaded into a 42 ml glass reactor for polymerization, equipped with magnetic stirring and opening for the loading and unloading of the reactants.

The so loaded reactor is cooled to $-196°$ C., evacuated, brought to room temperature and cooled again twice; at the end of this operation sequence the reactor is kept at 40° C. for 8 hours under magnetic stirring. The reaction crude product looks like a gelatinous mass. The reactor is brought to the temperature of the liquid nitrogen and connected to a vacuum system kept at the pressure of $10^{-3}$ mbar, it is then allowed to reach room temperature fractionating the vapours by traps cooled at $-80°$ C., $-120°$ C., and $-196°$ C.

The trap at $-80°$ C. contains only the $CFCl_2$—$CF_2Cl$ used as solvent. The trap at $-120°$ C. contains 4.90 moles of $CFCl_2$—$CF_2Cl$ and 0.16 moles of unreacted perfluorobisvinyloxymethane. The trap at $-196°$ C. contains 0.12 moles of unreacted tetrafluoroethylene.

After distillation of the solvent and of the unreacted monomers and stripping of the polymer under vacuum at the temperature of 120° C. for 3 hours, 1.030 g of polymer are isolated.

The weight balance made by gaschromatography analysis of the content of the traps containing the unreacted monomers allows to calculate the amount of perfluorobisvinyloxymethane in the polymer, which results to be 1.7% by moles.

The infrared analysis of the obtained polymer shows the absence of absorptions in the area of the carbonyl and of the fluorinated double bond.

The $\Delta H$ and the second melting point determined by DSC are respectively 9.8 cal/g and 314.5° C.

The TGA shows a weight loss of 2% at 502° C. and of 10% at 540° C. The polymer is hot moulded, at the temperature of 330° C. and at the pressure of 122 atm in a transparent and tough film.

EXAMPLE 30

Copolymer of perfluorobisvinyloxymethane with perfluorodioxole.

20 microliters of 6.5% by weight perfluoropropionylperoxide dissolved in $CCl_2F$—$CF_2Cl$, 2.95 moles of perfluorobisvinyloxymethane and 0.6 moles of perfluoro-1,3-dioxole are loaded into a 42 ml glass reactor for polymerization, equipped with magnetic stirring and opening for the loading and unloading of the reactants.

The so loaded reactor is cooled to $-196°$ C., evacuated, brought to room temperature and cooled again twice; at the end of this operation sequence the reactor is kept at 40° C. for 8 hours under magnetic stirring. The reactor is brought to the temperature of the liquid nitrogen and connected to a vacuum system kept at the pressure of $10^{-3}$ mbar, it is then let to reach room temperature fractionating the vapours by traps cooled at $-90°$ C., $-120°$ C., and $-196°$ C.

The trap at $-90°$ C. contains 1.92 moles of perfluorobisvinyloxymethane and $CFCl_2$—$CF_2Cl$ used as solvent. The trap at $-120°$ C. contains 0.22 moles of perfluorodioxole and 0.01 mmoles of perfluorobisvinyloxymethane. The trap at 196° C. contains 0.1 moles of perfluorodioxole.

After distillation of the solvent and of the unreacted monomers and stripping of the polymer under vacuum at the temperature of 120° C. for 2 hours, 280 mg of polymer are isolated.

The weight balance determined by gas chromatography analysis of the content of the traps containing the unreacted monomers allows to calculate the amount of perfluorobisvinyloxymethane in the polymer, which results to be 78% by moles.

The polymer $T_g$ determined by DSC is 94.5° C. The DSC graph does not show any melting endotherm, therefore the polymer is amorphous. The TGA shows a weight loss of 10% at 494° C.

EXAMPLE 31

Copolymer of bis (2-fluorovinyloxy)-difluoromethane with vinylidene fluoride.

1 ml of 6.5% by weight perfluoropropionylperoxide dissolved in $CCl_2F$—$CF_2Cl$, 10 ml of $CCl_2F$—$CF_2Cl$ and 1.5 g of bis (2-fluorovinyloxy)-difluoromethane (m.w.=172) are loaded into a 40 ml AISI-316 reactor for polymerization, equipped with magnetic stirring and opening for the loading and unloading of the reactants.

The so loaded reactor is cooled to $-196°$ C., evacuated, brought to room temperature and cooled again twice; at the end of this operation sequence the reactor is kept at 30° C.

and pressurized with vinylidene fluoride up to 20 atm. When the total pressure drops to 18 atm the reaction is blocked and gaseous reagents are removed at atmospheric pressure.

After distillation of the solvent and of the unreacted monomers and stripping of the polymer under vacuum at the temperature of 80° C. for 2 hours, 310 mg of polymer are isolated.

The polymer $T_g$ determined by DSC is 39.9° C. The DSC graph does not show any melting endotherm, therefore the polymer is amorphous. The TGA shows a weight loss of 6% at 300° C.

What is claimed is:

1. Polymers and copolymers of one or more fluorinated dienes of structure $CFX^1=CX^2-O-CX^3X^4-O-CX^2=CX^1F$, wherein $X^1$ and $X^2$, equal to or different from each other, are F, Cl or H, and $X^3$ and $X^4$, equal to or different from each other, are F or $CF_3$, said dienes essentially forming cyclic repetitive units having the structures:

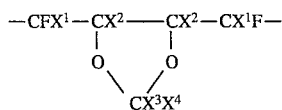  a)

and

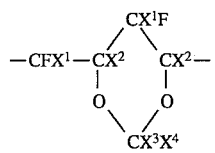  b)

wherein $X^1$, $X^2$, $X^3$ and $X^4$ have the meaning indicated above, at least one of the comonomers used in preparing said copolymers being a compound with an ethylene unsaturation having the structure:

$CY^1Y^2=CY^3Z$   c)

wherein $Y^1$, $y^2$, $y^3$, equal to or different from each other, are F, Cl or H and Z is F, Cl, H, $R^f$ or $O-R^f$ with $R^f$ perfluoroalkyl radical having from one to five carbon atoms, the compound containing at most 2 chlorine atoms; or

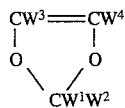  d)

wherein $W^1$ and $W^2$, equal to or different from each other, represent F or $CF_3$, $W^3$ represents F or H, and $W^4$ represents F, H, $R^f$ or $O-R^f$ with $R^f$ perfluoroalkylic radical containing from 1 to 5 carbon atoms.

2. Polymers and copolymers according to claim 1 wherein $X^2=X^1=F$.

3. Polymers and copolymers according to claim 2 wherein $X^2=X^1=F$.

4. Polymers and copolymers according to claim 3, wherein the fluorinated diene is $CF_2=CF-O-CF_2-O-CF=CF_2$ and the cyclic repetitive units derived from it have the following structures:

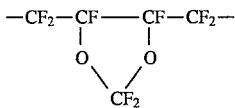  a)

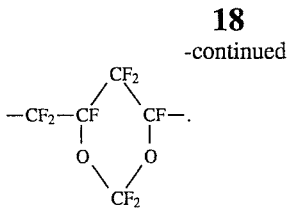  b)

5. Copolymers according to claim 1 comprising a comonomer selected from the group consisting of tetrafluoroethylene, vinylidene fluoride, ethylene, chlorotrifluoroethylene, trifluoroethylene, perfluoromethylcinylether, perfluoropropylvinylether, perflyoropropene, perfluoro 2,2-dimethyl-1,3-dioxole, perfluoro 1,3-dioxole and 2,2,4-trifluoro-5-trifluoromethoxy-1,3-dioxole.

6. Copolymers according to claim 5 wherein the comonomer is tetrafluoroethylene.

7. Copolymers according to claim 5 wherein the comonomer is vinylidene fluoride.

8. Copolymers according to claim 5 wherein the comonomer is selected from the group consisting of perfluoro 1,3-dioxole, perfluoro 2,2-dimethyl-1,3-dioxole and 2,2,4-trifluoro-5-trifluoromethoxy-1,3-dioxole.

9. A method for protecting articles used by the telecommunications industry for sending transmissions selected from the group consisting of metal wires and optical fibers, comprising:

coating said articles with polymers or copolymers of one or more fluorinated dienes of structure $CFX^1=CX^2-O-CX^3X^4-O-CX^2=CX^1F$, wherein $X^1$ and $X^2$, equal to or different from each other, are F, Cl or H, and $X^3$ and $X^4$, equal to or different from each other, are F or $CF_3$, said dienes essentially forming cyclic repetitive units having the structures:

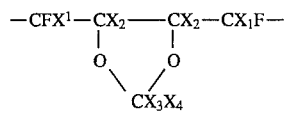  a)

and

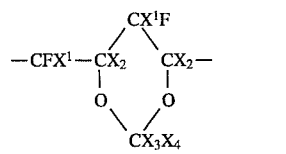  b)

wherein $X^1$, $X^2$, $X^3$ and $X^4$ have the meaning indicated above, at least one of the comonomers used in preparing said copolymers being a compound with an ethylene unsaturation having the structure:

$CY^1Y^2=CY^3Z$   c)

wherein $Y^1$, $Y^2$, $Y^3$, equal to or different from each other, are F, Cl or H and Z is F, Cl, H, $R^f$ or $O-F^f$ with $R^f$ perfluoroalkyl radical having from one to five carbon atoms, the compound containing at least 2 chlorine atoms, or

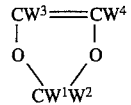  d)

wherein $W^1$ and $W^2$, equal to or different from each other, represent F or $CF_3$, $W^3$ represents F or H, and $W^4$ represents F, H, $R^f$ or $O-R^f$ with $R^f$ perfluoroalkylic radical containing from 1 to 5 carbon atoms.

* * * * *